United States Patent [19]
Muto

[11] Patent Number: 5,167,622
[45] Date of Patent: Dec. 1, 1992

[54] TRIPLE CONDUIT SUCTION CATHETER

[75] Inventor: Rudolph Muto, Andover, Mass.

[73] Assignee: Smiths Industries Medical Systems, Inc., Keene, N.H.

[21] Appl. No.: 623,339

[22] Filed: Dec. 7, 1990

[51] Int. Cl.$^5$ ............................................. A61M 1/00
[52] U.S. Cl. ........................................ 604/35; 604/43; 604/280
[58] Field of Search ................. 604/264, 35, 280, 281, 604/282, 283, 284, 24, 27, 35, 39, 43, 47; 128/207.14

[56] References Cited

U.S. PATENT DOCUMENTS

| | | |
|---|---|---|
| 1,211,928 | 1/1917 | Fisher . |
| 3,319,628 | 5/1967 | Halligan . |
| 3,429,313 | 2/1969 | Romanelli . |
| 3,599,641 | 8/1971 | Sheridan . |
| 3,906,954 | 9/1975 | Baehr et al. ............................ 604/27 |
| 4,014,333 | 3/1977 | McIntyre . |
| 4,022,219 | 5/1977 | Basta . |
| 4,036,210 | 7/1977 | Campbell et al. . |
| 4,139,012 | 2/1979 | Zahorsky . |
| 4,193,406 | 3/1980 | Jinotti . |
| 4,256,099 | 3/1981 | Dryden . |
| 4,294,251 | 10/1981 | Greenwald et al. . |
| 4,300,550 | 11/1981 | Gandi et al. . |
| 4,327,721 | 5/1982 | Goldin et al. . |
| 4,468,216 | 8/1984 | Muto . |
| 4,508,533 | 4/1985 | Abramson ............................ 604/35 |
| 4,595,005 | 6/1986 | Jinotti . |
| 4,696,305 | 9/1987 | von Berg . |
| 4,714,460 | 12/1987 | Calderon ............................ 604/264 |
| 4,881,542 | 11/1989 | Schmidt et al. . |
| 4,894,057 | 1/1990 | Howes ............................ 604/43 |
| 4,904,238 | 2/1990 | Williams ............................ 604/264 |
| 4,955,375 | 9/1990 | Martinez ............................ 604/280 |
| 4,968,249 | 11/1990 | Lohn . |
| 5,029,580 | 7/1991 | Radford et al. . |
| 5,033,466 | 7/1991 | Weymuller, Jr. ............. 128/207.14 |
| 5,073,164 | 12/1991 | Hollister et al. . |

FOREIGN PATENT DOCUMENTS 2053000  2/1981  United Kingdom .

OTHER PUBLICATIONS

Dennis, Clarence "The Gastrointestinal Sump Tube", Surgery, Aug. 1969, pp. 309-312.
Craig J. Bell Notebook page.

Primary Examiner—C. Fred Rosenbaum
Assistant Examiner—M. Mendez
Attorney, Agent, or Firm—Sewall P. Bronstein; Robert M. Asher

[57] ABSTRACT

A suction catheter provided with three conduits to provide th functions of suctioning, lavaging and oxygenating. The suction conduit is connected to a suction control member. The second conduit for the irrigating fluid is connected to a source of said fluid. The third conduit is connected to a source of gas under pressure. The gas conduit terminates within the irrigation conduit to form a common chamber at the distal end of the irrigation conduit from which fluid is propelled out by the pressurized gas. The gas may preferably contain oxygen.

10 Claims, 4 Drawing Sheets

TRIPLE CONDUIT SUCTION CATHETER

BACKGROUND OF THE INVENTION

The present invention is directed to a suction catheter suitable for use in removing undesirable fluid and debris from a patient.

Closed ventilation suction catheter systems, such as that available under the trade designation of STERICATH Model No. 6100 available from Smiths Industries Medical Systems, Inc. (SIMS), the assignee of the present invention, are presently in wide use. The closed ventilation suction catheter system includes a catheter-tube, crosspiece which connects to an endotracheal tube and also to a ventilating apparatus, a suction control member located at the end of the catheter tube opposite to that nearest the patient, a vacuum connection member located at the end of the suction control member, and a protective sleeve located between the crosspiece and the suction control member. Closed ventilation suction catheter systems make it possible to continue ventilation while at the same time applying suction to remove undesired accumulated fluid from a patient.

In removing fluid from a patient, it sometimes becomes necessary to provide a lavage solution to the patient, especially when tenacious mucous has built up. To accomplish this, the STERICATH Model No. 6100 catheter was a double lumen catheter in which one lumen provided suction while the other conveyed a lavage solution. The process of irrigating a patient with a lavage solution and suctioning out the undesired fluids can cause oxygen desaturation of the patient.

It is an object of the present invention to substantially reduce or eliminate the oxygen desaturation during suctioning while using an irrigating fluid. It is a further object of the invention to provide an oxygen-containing gas to propel the irrigating fluid out beyond the initial pull of the suction.

SUMMARY OF THE INVENTION

The present invention is directed to a suction catheter provided with a triple conduit catheter so as to simultaneously provide suctioning, lavage and oxygen.

The suction catheter includes three conduits carried by a catheter tube. A first elongated conduit has its proximal end connected to a suction control member. A second elongated conduit is connected to a source of liquid. A third elongated conduit is connected to a source of gas under pressure. The liquid in the second conduit is used to dislodge debris such as mucous from a patient's lungs so that the debris may be sucked through the suction conduit. The gas conduit preferably provides oxygen to replace oxygen which would otherwise be lost through the suction conduit.

Further, in accordance with the present invention, the gas conduit is combined with the irrigation conduit just prior to the irrigation conduit's distal end. In this manner, the pressurized oxygen-containing gas propels the irrigating fluid out of the catheter in a spray.

The present invention advantageously avoids the oxygen desaturation in the vicinity of the suctioning while still permitting the use of irrigating fluid to facilitate debris removal.

Other objects and advantages will become apparent during the following description of the presently preferred embodiments of the invention taken in conjunction with the drawings.

DETAILED DESCRIPTION OF THE PREFERRED EMBODIMENTS

Figure 1:
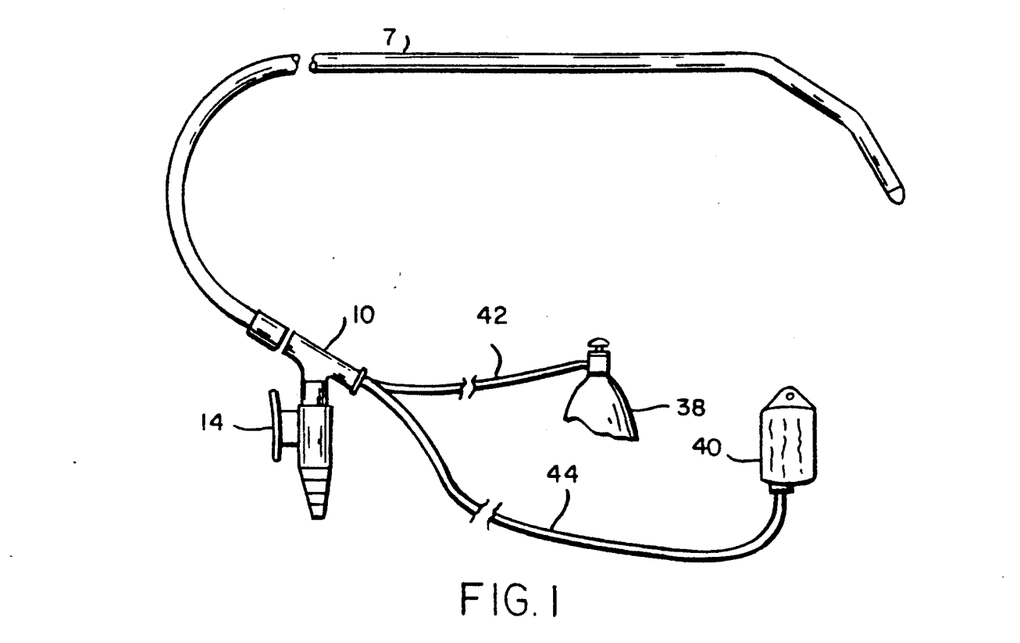
FIG. 1 is a perspective view of a suction catheter of the present invention.
Figure 2:
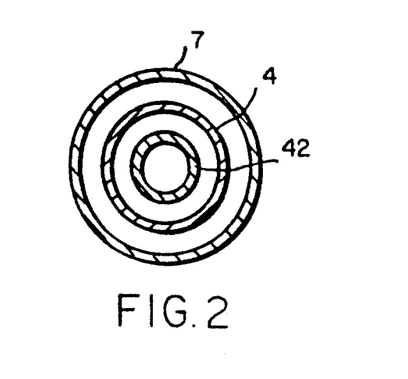
FIG. 2 is a cross-sectional view of the catheter tube of FIG. 1.

Referring now to the drawings, FIG. 1 illustrates a tracheal suction catheter using the triple lumen conduit of the present invention. An outer suction catheter tube 7 is connected to a Y connector 10 at its proximal end. The Y connector includes an arm for connection to a vacuum source (not shown). This arm may include a control mechanism for controlling the application of suction through the suction catheter. A simple vent hole 14 (thumb port) operable by a health care personnel's thumb is sufficient. A second arm of the Y connector 10 connects with irrigation tubing 44. The irrigation tubing 44 is connected to a fluid source such as a bag of saline solution hanging from an IV pole. The irrigation tubing 44 is inserted through the length of the suction catheter tube 7. The distal end of the irrigation tube expels irrigating fluid and the suction catheter 7 provides suction for retrieving the fluid and debris, mucuous or secretions that are loosened. In accordance with the present invention, a gas catheter tube 42 is inserted in through the irrigation tubing 44. The gas tube 42 travels concentrically within both the irrigation tubing and the suction tube 7. The proximal end of the gas catheter tube 42 is connected to a source of pressurized gas, preferably an oxygen-containing gas. The concentric arrangement of the three tubes are shown in FIG. 2. In accordance with a presently preferred embodiment, the suction catheter tube 7 has an outer diameter of 0.18 in. and an inner diameter of 0.108 in. The irrigation tube 44 has an outer diameter of 0.65 in. and an inner diameter of 0.53 in. The gas catheter tube 42 has an outer diameter of 0.28 in. and an inner diameter of 0.20 in.

Figure 3:
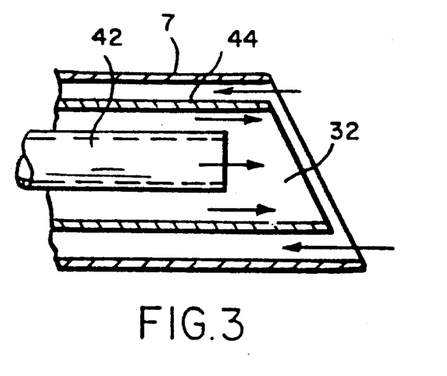
FIG. 3 is a longitudinal cross-section of the outlet portion of the catheter tube of FIG. 1.

The outlet end of the catheter tubes are shown in FIG. 3. In accordance with the present invention, the gas lumen is set back within the irrigation lumen. Thus, in the distal end of the irrigation lumen, a common chamber 32 is formed in which the pressurized oxygen drives the fluid out of the catheter far enough so that it enters the patient cavity before returning back through the suction portion of the catheter. The intermixing of the oxygen and irrigation fluid may also aid in providing a spray of fluid out through the end of the catheter. The oxygen thus advantageously acts as a propellant. This permits the irrigation tubing to lie back within the suction catheter tube 7 so as not to scratch any tissue within the patient cavity, i.e., the lungs for the tracheal device. The oxygen being supplied also serves the function of replacing oxygen which is lost from the lungs due to the suctioning through the catheter tube 7. The catheter of the present invention may be inserted into a patient through a peep keep or other commonly used device which permits ventilation of the patient to continue during the irrigating and suctioning operation.

Figure 4:
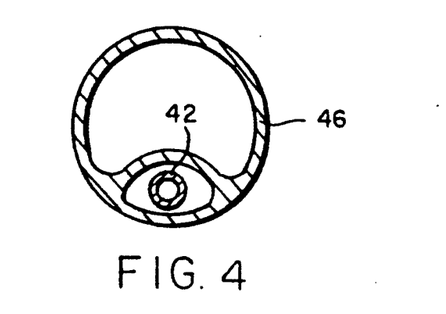
FIG. 4 is a cross-sectional view of three conduits in an alternate embodiment of the suction catheter of the present invention.
Figure 5:
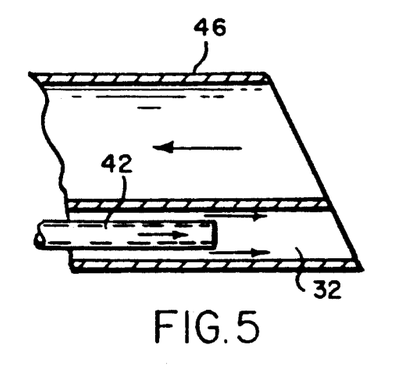
FIG. 5 is a longitudinal cross-sectional view of the outlet portion of the catheter tube of FIG. 4.

In accordance with FIG. 4, an alternate embodiment is shown for providing three conduits through the suction catheter tube. The outer tube is a double lumen catheter 46 having its larger conduit for use in suctioning and a second conduit for use by the irrigating fluid. The second conduit is large enough so as to accomodate an oxygenation single catheter tube 42. One arm of the Y-connector 10 provides suction to the large conduit. The second arm of the Y-connector provides irrigating fluid into the second conduit. The oxygen tube 42 is inserted through the irrigation conduit. FIG. 5 shows the distal end of this suction catheter. In order to drive the irrigating fluid out in a spray the oxygen tube terminates back from the end of the irrigation conduit to form a common chamber 32.

Figure 6:
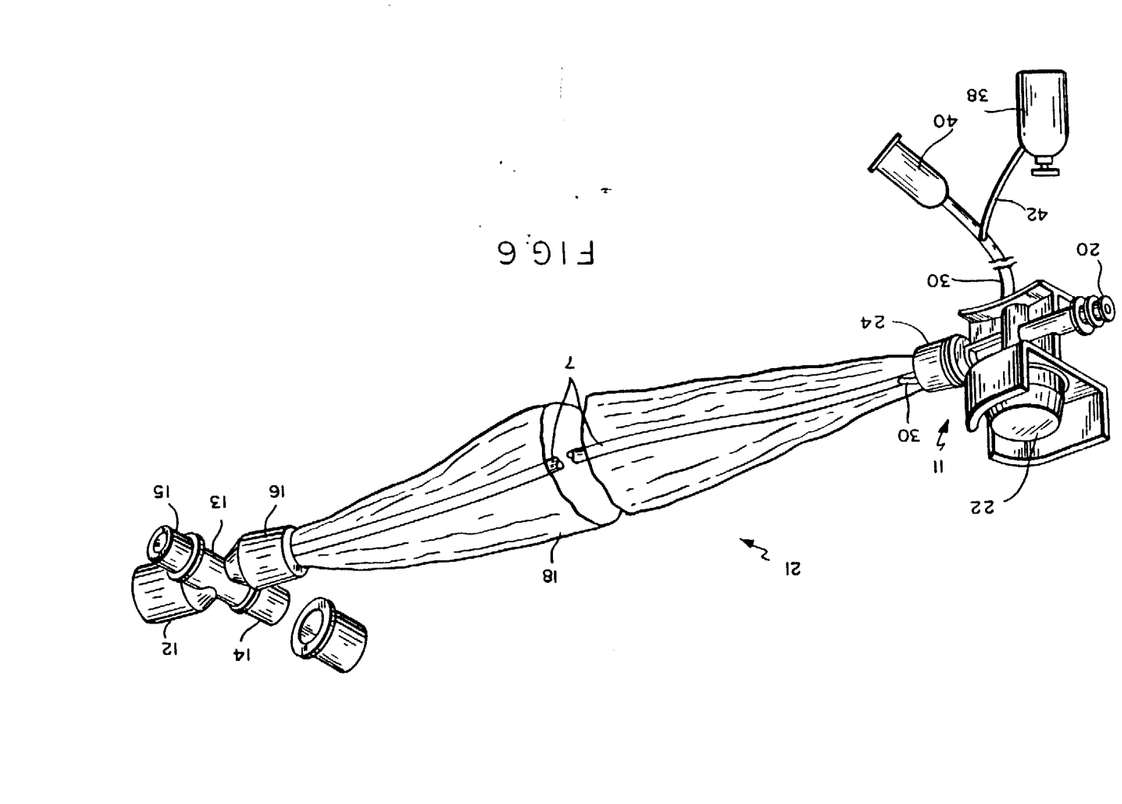
FIG. 6 is a perspective view of a suction catheter in a closed ventilation system of the present invention.

FIG. 6 illustrates a suction catheter in a closed ventilation assembly 21. The closed assembly 21 includes a catheter tube 7 which extends from its proximal end in a suction control member 11 down to its distal end where it either sticks out of or is surrounded by a patient cross piece or respiration intersection piece 13. The catheter tube 7 can be slid back and forth through the patient cross piece 13. (Tee-pieces, Y-pieces, etc. can also be used.) The cross piece has an output port 12 which is provided for connection to a suitable connecting element to a patient, such as an oral and/or nasal connecting element and particularly an endotracheal or tracheostomy connector (not shown). The ports 14 and 15 of the patient connection member 13 are provided for connection to a ventilating apparatus (not shown) via an input tube (not shown) and a return tube (not shown) as known in the art. A port 16 extending from the patient connection member in the direction of the proximal end of the catheter tube is connected to a protective sleeve 18.

The catheter tube 7, at its distal end, passes through the cross piece 13 through a wiper seal located in the extension 16 from the member and surrounding the periphery of the catheter tube. The wiper seal can be made of a silicone rubber material.

The proximal end of the catheter tube is connected to a suction control member 11. The suction control member 11 includes an outlet 20 for connection to a vacuum source (not shown). The vacuum connection member 11 includes a bore of the same size as the inside diameter of the conduit in the catheter tube 7 for providing suction. The vacuum connection member 20 is normally made of a relatively rigid material such as SAN (polymer of styrene and acrylonitrile). Also located on the suction control means 11 is a valve member 22. The valve member 22 illustrated is a spool type valve preferably made of butyl rubber. The valve is operated by manually applying a force to the top of the valve rubber member whereby the valve is pushed down such that it no longer blocks the passageway to the catheter tube and thereby suction can be applied from the vacuum source. Upon release of the manual force, the valve returns to its normal resting position in which the vacuum source is sealed from the catheter tube 7. Other suction control means can also be used, e.g., the aforesaid thumb port, a clamp, etc.

The protective sleeve 18 surrounds at least the majority of the length of the catheter tube 7. The protective sleeve 18 is adapted to permit the distal end of the catheter tube to be extended from the protective sleeve into a patient and to be withdrawn from the patient. The flexible protective sleeve is generally cylindrical in shape and is formed of a flexible, lightweight, translucent plastic material such as a high clarity polyethylene with a typical thickness of about 0.002 inches. The ends of the protective sleeve 18 are adhesively secured to the port 16 of the patient cross piece member and at its other end to a port 24 of the suction control member. The connection with the port 16 and port 24 can be made by providing each port with a threaded collar which is twisted onto a mating externally threaded portion of the patient cross piece member and suction control member, respectively, with the end of the protective sleeve 18 and an adhesive located between the collars and the externally threaded portions. A typical adhesive is polyvinylchloride doped tetrahydrofuran.

In accordance with the present invention, three elongated conduits are provided through catheter 7. The larger conduit connects through valve 22 to the vacuum source and is thus used for suction. A second conduit is connected to a source 40 of liquid lavage solution. Typically, the lavage solution is a saline solution. A third conduit is connected to a source 38 of pressurized oxygen.

Figure 7:
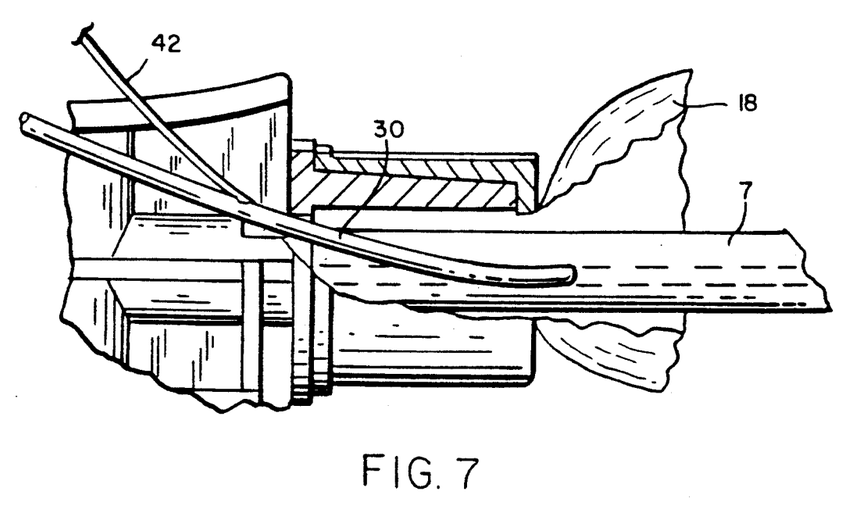
FIG. 7 is a partial cross-sectional view of a portion of the suction catheter of FIG. 6 where the three conduits enter the device.
Figure 8:
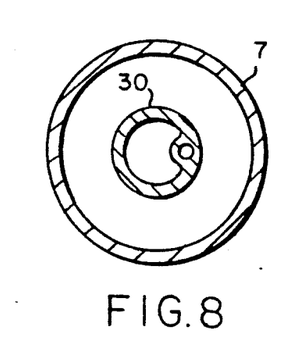
FIG. 8 is a cross-sectional view of a second alternate catheter tube as illustrated for use in the embodiment of FIG. 6.

Several embodiments for providing three conduits have been devised. In addition to the two embodiments described above which are equally applicable to a closed system, we turn now to FIGS. 7 and 8. The first flexible elongated catheter 7 is connected to the suction control member 11. This first catheter forms the largest of the conduits for suctioning. A second catheter 30 is inserted into the catheter 7 through a hole in its side. Preferably, the hole is located within the area guarded by the shield 18. The catheter 30 in accordance with this embodiment, is a double lumen catheter. The larger lumen of catheter 30 is used for lavage solution. The smaller lumen is used for pressurized oxygen. An oxygen connection tube 42 is provided for insertion into the double lumen catheter 30 so as to provide connection between the oxygen lumen and a source of pressurized oxygen. The double lumen catheter 30 extends the full length of the catheter tube 7 so that the distal ends approximately coincide.

Figure 9:
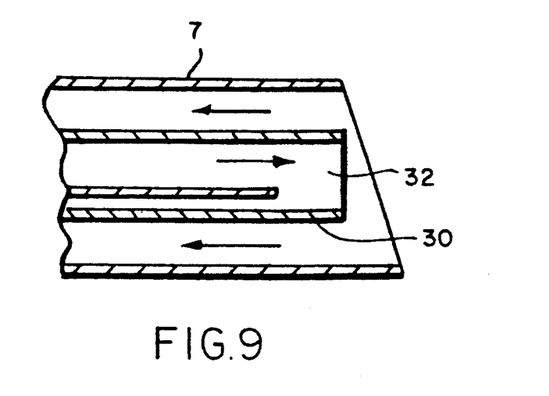
FIG. 9 is a longitudinal cross-sectional view of the outlet portion of the catheter tube of FIG. 8.

Referring now to FIG. 9, the distal end of this catheter embodiment with the double lumen catheter inside the suction catheter 7 is shown. In order to obtain a common irrigating chamber 32 within the double lumen catheter 30, the inner wall of the lumen which forms the oxygen lumen is stripped away at its distal end. Stripping the lumen wall back about a half an inch is adequate to create a chamber 32 in which the oxygen drives the irrigating fluid out from the catheter in the form of a spray. Thus, the oxygen can aid in propelling the irrigating fluid beyond the initial pull of the suction so that the fluid enters the patient cavity before returning through the suction line along with secretions, debris and mucous.

Figure 10:
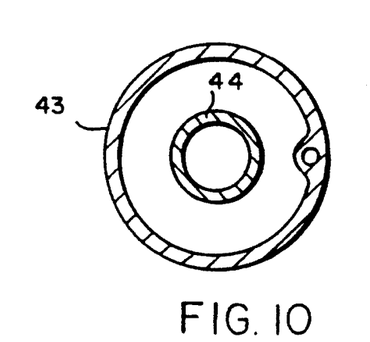
FIG. 10 is a cross-sectional view of a third alternate catheter tube.
Figure 11:
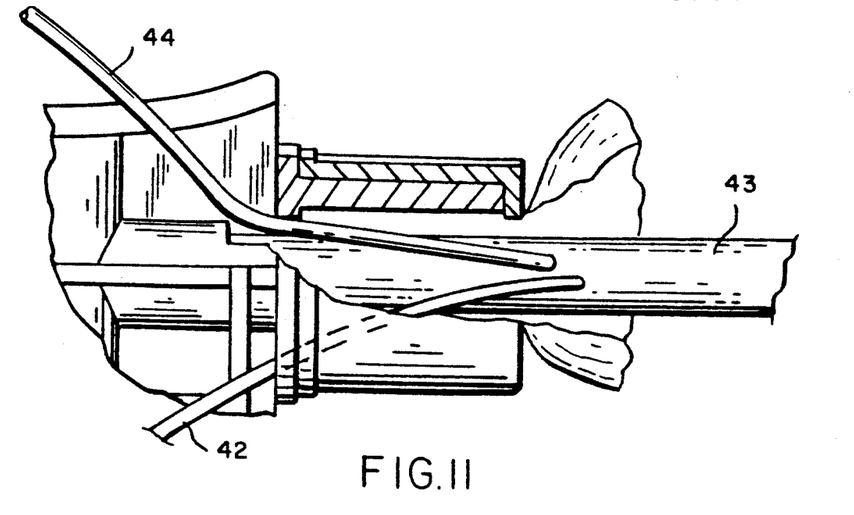
FIG. 11 is a partial cross-sectional view of the portion of a suction catheter where the three conduits of FIG. 10 enter the device.

Referring to FIGS. 10 and 11, a further alternate embodiment is shown in which a double lumen catheter tube 43 has a large lumen connected to the vacuum source for suctioning. The double lumen catheter 43 has a smaller lumen for oxygenation. The connection tube 42 shown in FIG. 11 extends the oxygenation conduit to provide connection to a source 38 of pressurized oxygen. Connection tube 44 is a single lumen catheter tube for connection to a source 40 of lavage solution/ This tube is inserted through a hole in the side of the double lumen catheter 43. The catheter tube 44 extends the full length of the double lumen catheter tube 43 so that the lavage solution is expelled into the lung cavity to break up and moisturize mucous so that it can be suctioned back through the suction conduit. The solution also serves to irrigate the suction conduit. The embodiment oxygenates the area being suctioned but lacks the advantage of using the oxygen as a propellant. Therefore, it may be necessary to have the irrigation tube 44 extend out beyond the distal end of the double lumen suction tube 43.

Figure 12:
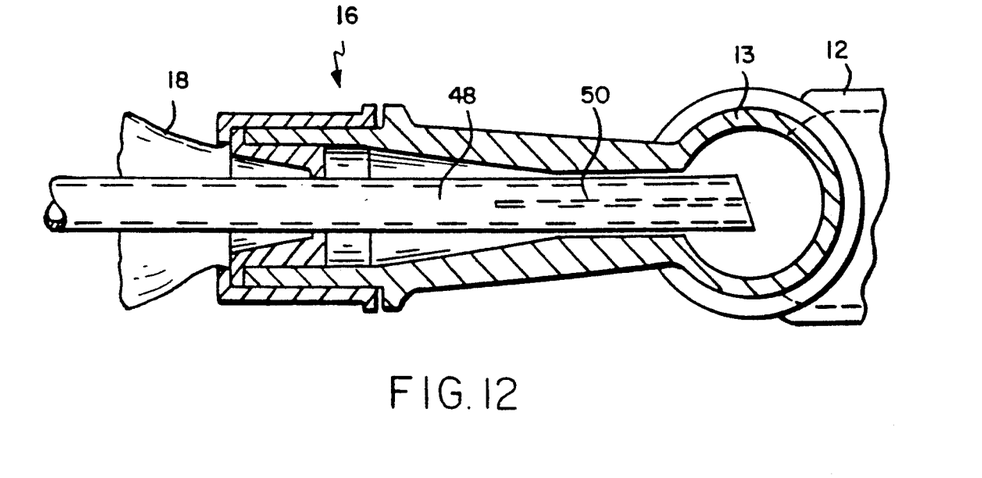
FIG. 12 is a cross-sectional view at the respiration intersection piece for a fourth alternate catheter tube of the present invention.
Figure 13:
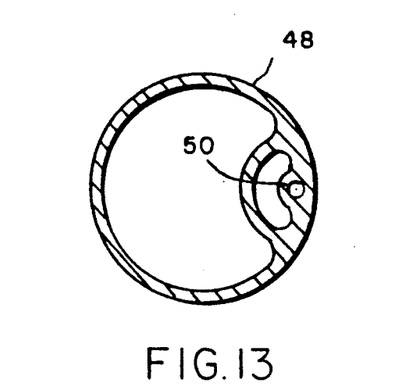
FIG. 13 is a cross-section of the catheter tube of the embodiment of FIG. 12.

A still further embodiment is shown in FIGS. 12 and 13 in which a triple lumen catheter 48 provides the three conduits for the suction catheter. The largest lumen is used for suction, the second largest lumen is used for lavage solution and the small lumen is used for the oxygen. Near the proximal end of the catheter 48, connector tubes are inserted into the side of the catheter to provide connections between the lumens and the lavage solution and pressurized oxygen. The common irrigating chamber can be formed by cutting a slit 50 in the wall separating the oxygen lumen from the lavage solution lumen extending about a quarter inch to about one half inches in length from the distal end of the catheter. Alternatively, the separating wall can be removed in the last quarter inch to one-half inch of the catheter. The common chamber enables the pressure from the oxygen gas to drive the irrigating fluid beyond the force of the suction. This better ensures that the irrigating fluid is actually used to hit the mucous and break it up rather than being first sucked in through the suction lumen. The multilumen catheter is preferably made from PVC tubing.

The closed ventilation assembly is used by connecting the cross piece member 13 to the patient and then inserting the three conduit catheter tube into the patient cavity, normally the trachea. Lavage solution is expelled into the patient's trachea so as to dislodge and moisturize debris such as mucous from a patient's lungs. The vacuum source attached to the vacuum connection member sucks the dislodged debris and lavage solution up through the larger conduit away from the trachea. Advantageously, oxygen which is removed by the suction of the vacuum source is replenished by the oxygen provided through the third conduit. Also, the oxygen can be used to spray the irrigating fluid into the cavity. This extends the range of fluid which flows in a vortex out into the cavity and back through the suction conduit. This flow continues to be pulled through the suction conduit as in a siphon. The additional range is useful in keeping the end of the suction conduit away from the tissue in the cavity which would be pinched and irritated if sucked onto the end of the tube. While this lavaging, suctioning and oxygenating is being performed, the patient may be respirated with the help of a ventilator connected to the ports 14 and 15 of the cross piece. Thus, while the patient is generally receiving oxygen through respiration, the oxygen conduit provides oxygen directly to the area in the lungs where suctioning is taking place. Thus, the localized loss of oxygen is avoided or at least significantly diminished. If a patient is not being respirated during suctioning the simultaneous provision of oxygen achieved in the present invention has the added importance of being the only source of oxygen to the lungs.

While the preferred embodiments of the present invention have been illustrated and described, it will be appreciated that various changes can be made therein without departing from the spirit and scope of the present invention.

I claim:

1. A suction catheter comprising:
    a flexible catheter tube;
    a first flexible elongated conduit extending longitudinally within said catheter tube having a distal end with a debris receiving suction inlet opening and a proximal and;
    means for coupling the proximal end of said first conduit to a vacuum source;
    a second flexible elongated conduit extending parallel to said first elongated conduit within said catheter tube from a distal end of said second conduit to a point where said second conduit is directed away from said first conduit and into connection with a source of liquid at a proximal end of said second conduit;
    a chamber in the distal end of said second elongated conduit for receiving liquid from said second elongated conduit; and
    a third flexible elongated conduit being smaller in diameter than said first elongated conduit and said second elongated conduit, extending parallel to said first and second elongated conduits within said catheter tube from a distal end with a gaseous outlet to a point where said third conduit is directed away from said first and second conduits and into connection with a source of gas under pressure at a proximal end of said third conduit, said gaseous outlet opening into said chamber such that gas exiting from said third conduit through said outlet enters said chamber to drive the liquid out of said chamber.

2. The suction catheter of claim 1 wherein the gas comprises oxygen.

3. The suction catheter of claim 1 wherein said flexible catheter tube is a double lumen catheter, said first and second flexible elongated conduits forming lumens next to one another in said catheter and further wherein said third flexible elongated conduit is contained within a catheter inserted through said second elongated conduit.

4. The suction catheter of claim 1 wherein said flexible catheter tube is a single lumen catheter forming said first conduit and each of said second and third conduits has an outer wall formed by a single lumen catheter.

5. The suction catheter of claim 4 wherein said second conduit surrounds said third conduit.

6. The suction catheter of claim 1 wherein said coupling means comprise a Y-connector having one arm connected to the vacuum and a second arm connected to said second and third elongated conduits.

7. A suction catheter comprising:
- a first catheter tube having a cylindrical outer wall;
- a first conduit extending through said first catheter tube having a distal end with a suction inlet opening and a proximal end;
- means for coupling the proximal end of said first conduit to a vacuum source;
- a second conduit extending through said first catheter tube having a distal end with a fluid outlet opening and a proximal end;
- means for coupling the proximal end of said second conduit to a fluid source;
- a third conduit extending longitudinally through said first catheter tube having a distal end with a gaseous outlet opening and a proximal end;
- means for coupling the proximal end of said third conduit to a source of gas under pressure; and
- a common chamber in the distal end of said second conduit formed by having the distal end of said third conduit opening into said common chamber so that the gas from said third conduit propels the fluid from said second conduit out of the chamber.

8. The suction catheter of claim 7 wherein said gas comprises an oxygen-containing gas.

9. The suction catheter of claim 7 wherein said first catheter tube is a double lumen catheter wherein said first and second conduits form lumens next to one another in said catheter and wherein said third conduit is contained within a catheter inserted through said second conduit.

10. The suction catheter of claim 7 wherein said first catheter tube forms said first conduit, a second catheter tube inserted within said first catheter tube forms said second conduit and a third catheter tube inserted within said second catheter tube forms said third conduit.

* * * * *

UNITED STATES PATENT AND TRADEMARK OFFICE
CERTIFICATE OF CORRECTION

Page 1 of 2

PATENT NO. : 5,167,622
DATED : December 1, 1992
INVENTOR(S) : Rudolph Muto

It is certified that error appears in the above-identified patent and that said Letters Patent is hereby corrected as shown below:

IN THE DRAWINGS

Delete Sheet 2 of 4 showing Figs. 4 and 5 (drawings of teeth), which were erroneously included in the patent, and substitute therefor Sheet 2 of 4 showing Fig. 6 (copy attached hereto), which was included in the original application as filed.

ON THE COVER SHEET

Delete:

"Assignee: Smiths Industries Medical Systems, Inc., Keene, N.H."

Signed and Sealed this

Twenty-sixth Day of April, 1994

BRUCE LEHMAN

*Attest:*

*Attesting Officer*   Commissioner of Patents and Trademarks

FIG. 6

UNITED STATES PATENT AND TRADEMARK OFFICE
CERTIFICATE OF CORRECTION

PATENT NO. : 5,167,622
DATED : December 1, 1992
INVENTOR(S) : Rudolph Muto

It is certified that error appears in the above-indentified patent and that said Letters Patent is hereby corrected as shown below:

On the title page: Item [73]

Delete Assignee: Smiths Industries Systems Inc., Keene, N. H.

Signed and Sealed this

Twenty-sixth Day of July, 1994

Attest:

BRUCE LEHMAN

*Attesting Officer*  *Commissioner of Patents and Trademarks*